United States Patent [19]

Beiner et al.

[11] 4,406,660

[45] Sep. 27, 1983

[54] NON WOVEN FABRICS SUITABLE FOR DIAPER AND DIAPER COVERSTOCK

[75] Inventors: Jean-Marc Beiner, Antibes; Jerome F. Levy; Bernard J. M. Sweens, both of Biot, all of France

[73] Assignee: Rohm and Haas Company, Philadelphia, Pa.

[21] Appl. No.: 206,759

[22] Filed: Nov. 14, 1980

Related U.S. Application Data

[63] Continuation of Ser. No. 98,583, Nov. 29, 1979.

[30] Foreign Application Priority Data

Dec. 4, 1978 [GB] United Kingdom .............. 47036/78
Dec. 20, 1978 [GB] United Kingdom .............. 49235/78

[51] Int. Cl.³ ............................................. A61F 13/16
[52] U.S. Cl. .................................... 604/376; 428/288; 428/289; 428/290; 428/913; 526/317
[58] Field of Search .............. 428/289, 290, 913, 288; 260/29.6 TA; 526/317; 128/284; 604/367, 372, 375, 376

[56] References Cited

U.S. PATENT DOCUMENTS

| | | | |
|---|---|---|---|
| 2,931,749 | 4/1960 | Kine et al. | 154/101 |
| 3,020,178 | 2/1962 | Sweeney et al. | 117/155 |
| 3,157,562 | 11/1964 | Kine et al. | 161/170 |
| 3,554,788 | 11/1971 | Fechillas | 117/140 |
| 3,616,166 | 10/1971 | Kelley | 161/148 |
| 4,148,987 | 4/1979 | Winey | 526/316 |
| 4,356,229 | 8/1981 | Brodnyan et al. | 428/297 |

FOREIGN PATENT DOCUMENTS 1478522 7/1977 United Kingdom .

*Primary Examiner*—James J. Bell
*Attorney, Agent, or Firm*—Harold L. Greenwald; Michael B. Fein

[57] ABSTRACT

Non-woven fibrous products, such as diapers, in which the fibres are bound together by an emulsion copolymer of $C_4C_8$ ester of acrylic and/or methacrylic acid: at least one of methyl methacrylate, styrene or α-methyl styrene and acid comprising mono-unsaturated dicarboxylic acid optionally in combination with mono-unsaturated monocarboxylic acid. The fibres comprise at least 50% hydrophilic fibres such as cellulosic fibres.

9 Claims, No Drawings

NON WOVEN FABRICS SUITABLE FOR DIAPER AND DIAPER COVERSTOCK

This is a continuation, of application Ser. No. 98,583, filed Nov. 29, 1979.

The field of this invention is non woven materials. This invention is concerned with non-woven fibrous materials containing hydrophilic fibres bound together by certain polymers.

Greater attention is now being paid to the impact on health and environment of the components of santiary and health care fabrics such as diapers, sanitary napkins, hospital curtains, disposable sheets and bed pads. Non-woven fabrics for these applications are also required to have adequate tensile strength and abrasion resistance, when wet by water or aqueous liquids such as body fluids. Generally the binders in current use for non-wovens are crosslinked in order to obtain adequate wet strength and abrasion resistance.

Usually the crosslinking is based on formaldehyde, a noxious material known to be a skin irritant and also possibly carcinogenic. This type of crosslinking involves the reaction of methylol groups in the polymer, such as N-methylolacrylamide or the reaction of added aminoplasts such as methylolated melamine or urea formaldehyde. This type of crosslinking is thought to be instrumental in achieving suitable wet strength in non-wovens. Such systems are described in U.S. Pat. Nos. 2,931,749 and 3,157,562. For similar health reasons it is desirable that the binder be free from other materials such as acrylonitrile.

We have now found certain binder polymers substantially free from methylol group-containing units and added aminoplast which, surprisingly, substantially retain in non-wovens containing hydrophilic fibres the wet strength conferred by similar methylol-containing polymers.

An important application of non-woven fabrics is in the manufacture of diapers. Hitherto hydrophilic fibres, such as cellulosics and in particular rayon, have enjoyed a large share of the non-wovens used for diapers. This is because hydrophilic fibres are absorbent. Now, however, diaper coverstock is being constructed from non-wovens which allow easy passage of body fluids into the diaper, known as strikethrough, but deter passage of the fluids from the diaper, known as wetback. Such diapers are constructed from hydrophobic fibres, such as polyester. However, there is still a considerable market for hydrophilic fibres and it is desirable to adapt hydrophilic fibres to perform in much the same way as hydrophobic ones.

We have now found certain binder polymers which can provide a desirable balance of strikethrough and wetback properties in non-wovens containing hydrophilic fibres.

Diapers often comprise an envelope known as coverstock which, during manufacture, is sealed by the application of heat. Non-wovens bound by conventional crosslinked polymers are difficult to seal; they have poor heatsealability. This can be a significant disadvantage.

We have now found certain binder polymers which can confer upon non-wovens containing hydrophilic fibres improved heatsealability.

In the process of making non-woven products binder polymers can cause an undesirable degree of adhesion to the processing equipment. Clearly this impedes a smooth running operation. This characteristic is known as runnability.

We have now found certain binder polymers which may have good runnability properties.

According to the invention there is provided a non-woven fibrous product whose fibres comprise at least 50%, by weight of dry fibre weight, of hydrophilic fibres in which the fibres are bonded together by an emulsion copolymer of:

(a) 50–80%, preferably 60–80%, by weight of at least one $C_4$–$C_8$ ester, preferably $C_4$–$C_8$ alkyl ester, of acrylic and/or methacrylic acid, such as butyl acrylate and 2-ethylhexyl acrylate;

(b) 10–49%, preferably 15–30%, by weight of at least one of methyl methacrylate, styrene and α-methyl styrene, preferably styrene; and (c) 0.5–10%, preferably 1–10%, more preferably 1–6%, by weight of acid comprising at least one monoethylenically unsaturated dicarboxylic acid, optionally in combination with at least one monoethylenically unsaturated monocarboxylic acid.

By hydrophilic fibres we means fibres which, when dry, have a moisture regain at 21.1° C. (70° F.) and 65% relative humidity of more than $2\frac{1}{2}\%$. (See Textile World, August 1978, p 51 et seq).

Preferably the fibres of the non-woven product of this invention comprise at least 50% by weight of dry fibre weight of cellulosic fibres, such as rayon, and the balance may be one or more other natural or synthetic fibres. Blends of 50% rayon and 50% polyester are preferred with 100% rayon more preferred.

The copolymer may contain small amounts such as up to 10%, preferably 5%, by weight of units of other functional monomers such as hydroxyethyl acrylate or methacrylate, hydroxypropyl acrylate or methacrylate, acrylamide or methacrylamide or mixtures of such monomers. However, the copolymer should be substantially free from units containing methylol groups and from added aminoplasts. It is preferred that the copolymer does not contain additional functional units and more preferred that it consists substantially of units of categories (a), (b) and (c) above.

Acid component (c) may comprise dicarboxylic acids such as itaconic or maleic acid and optionally monocarboxylic acids such as acrylic or methacrylic acid. Preferably (c) comprises 0.5–3%, more preferably 0.75–3%, dicarboxylic acid optionally with 0.5–3%, more preferably 0.75–3%, monocarboxylic acid. Itaconic acid is preferred for improved wet strength.

In a preferred embodiment of this invention the binder copolymer contains units of both at least one dicarboxylic acid and at least one monocarboxylic acid, as described above.

We have found, surprisingly, that polymers containing both types of acids generally provide better wet strength in the non-woven than either acid alone.

Therefore component (c) above preferably comprises itaconic acid and acrylic and/or methacrylic acid.

In addition we have found that this combination of acids enhances the runnability properties provided by itaconic acid alone. The combination of itaconic acid and acrylic acid is preferred for a desirable balance of improved wet strength and runnability over individual acids.

In the acid mixtures, the weight ratio of dicarboxylic to moncarboxylic acids is preferably from 4:1 to 1:4, more preferably from 2:1 to 1:2.

Acid component (c) may be in the form of free acid or may be in the form of a salt with for example, an alkali metal, such as sodium or potassium, a water soluble amine, such as methylamine, diethylamine, triethylamine, mono- di- or tri-ethanolamine or morpholine, or in the form of an ammonium salt.

The non-woven products of this invention are particularly useful in the manufacture of diapers. Accordingly further preferred embodiments of this invention provide diaper coverstock and finished diapers comprising the non-woven products described herein.

Non-woven fibrous products according to the invention may be formed in any suitable manner such as by carding, garnetting, or by dry deposition from an air suspension of the fibres. When the fibrous product is formed by carding or garnetting, the fibres are usually at least partially orientated whereas in products formed by air deposition the fibres are in a completely haphazard distribution. A thin web or fleece obtained from a single card may be treated with the copolymers described herein, but generally it is necessary and desirable to superimpose a plurality of such webs to build up the mat to sufficient thickness for the end use intended. In building up such a mat alternate layers of carded webs may be disposed with their fibre orientation directions disposed at 60° or 90° angles with respect to intervening layers.

The copolymer may be applied to the fibres as an aqueous dispersion in any suitable fashion such as by spraying, dipping or roll-transfer. The concentration of copolymer in the dispersion may be from 5% to 60% by weight, and preferably from 5% to 25%, at the time of application as an aqueous dispersion.

The binder dispersion or powder may be applied to the dry fibres after the formation or deposition of the web or mat so as to penetrate partially into or completely through the interior of the fibrous products. Alternatively, the binder dispersion or powder may be applied to the fibres as they fall through the settling chamber to their point of deposition. This is advantageously obtained by spraying the binder dispersion or powder into the setting chamber at some intermediate point between the top and the bottom thereof. By so spraying the fibres as they descend to the point of collection, it is possible to effect a thorough distribution of the binder among the fibres before they are collected into the product. In the production of certain fibrous products wherein a hot molten mass of a polymer is disrupted by jets of heated air or steam, the binder dispersion or powder may be sprayed directly on the fibres while still hot and very shortly before their deposition so that quickly after deposition the binder is set and bonds the fibres in proper relationship. Preferably, however, application of the binder dispersion to the fibrous product is made at room temperature to facilitate cleaning of the apparatus associated with the application of the binder dispersion. The binder dispersion may be applied to one or both surfaces of the fibrous product or it may be distributed through the interior as well.

The binder of the present invention may be applied in conjunction with other binders, such as glue. Similarly, the use of potentially adhesive fibres within the fibrous product may also be resorted to in conjunction with the use of the polymeric binder.

If desired, there may be used an aqueous polymer dispersion which also contains a wetting agent to assist penetration of the fibrous web or mat to which it is applied, and it may contain either a foaming agent to provide the binder in a foamed condition in the final product or it may contain a defoamer when the ingredients of the aqueous dispersion have a tendency to give rise to foaming and in a particular case such foaming is undesirable. The conventional wetting agents, such as the sodium salt of dioctylsulfosuccinic acid, may be used and the conventional foaming and defoaming agents may be employed, such as sodium soaps, including sodium oleate for foaming the octyl alcohol or certain silicones for defoaming.

The proportion of the polymer that is applied to the wet or mat is such as to provide 15 to 50% (or, in some cases, even up to 75%) by weight of copolymer based on the total weight of copolymer and fibres. After application of the aqueous dispersion of the water-insoluble copolymer to the fibrous web, the impregnated or saturated web is dried either at room temperature or at elevated temperatures.

The binder copolymers used in this invention may be prepared by conventional emulsion copolymerisation processes, such as are described in U.S. Pat. Nos. 2,754,280 and 2,795,564, employing a suitable emulsifier such as a non-ionic, cationic, or an anionic emulsifier or mixtures of a non-ionic with a cationic or an anionic emulsifier in conjunction with a free-radical initiator which may, if desired, be a component of any of the well known redox systems. Examples of emulsifiers that may be used include sodium lauryl sulphate, t-octylphenoxypolyethoxyethanols containing from about 10 to 50 oxyethylene units per molecule, and lauryl pyridinum chloride. The amount of emulsifier may range from about ½% to 6% on the weight of monomers. Any free-radical initiator such as azodiisobutyronitrile, t-butyl hydroperoxide, and ammonium or potassium persulphates may be employed. The proportion of initiator may be from 0.1% to 2% on the weight of monomers.

Some preferred embodiments of the invention will now be more particularly described in and by the following examples, in which all percentages are by weight and all temperatures in °C., unless otherwise stated.

EXAMPLES 1-27

Non-woven fabrics are prepared from 100% rayon bound by the polymers specified in Table 1.

Comparative examples 1-6 show the performance of a methylol-crosslinking binder and binders free from such groups but containing no dicarboxylic acid. The latter binders have lower wet strength and generally poor runnability. The other examples in the Table describe non-wovens according to the invention in which the binder contains a dicarboxylic acid. These materials have improved wet strength.

In Table 1 the following test methods are used:

TENSILE STRENGTH 22-23% solids of the binder are applied by impregnation on a directional laid rayon non-woven web (about 31.5 g/m$^2$). The non-woven sample (about 39.5 cm × 26.5 cm) is weighed before impregnation and inserted in a cotton/Dacron 54 (35/65) fabric. Impregnation is carried out at about 12.5% solids in the bath. The sample is weighed again and dried in a Werner Mathis oven type LTF No 1268. The drying and curing conditions are 2 minutes at 150° C.

The impregnated non-wovens are conditioned overnight at 20° C.±1° C. and 65%±10 relative humidity before testing.

2.5 cm wide samples are tested on an Instron machine with an opening between the jaws of 10 cm. Tests are made dry and wet, after soaking the samples for 10 minutes in water. Results are an average of 10 tests with Instron settings of paper speed 20 cm/min. and machine speed 50 cm/min.

Desirable tensile and heat sealability values under wet conditions are 320 g/2.5 cm and 150 g/5 cm respectively.

TABLE 1

| Example | Monomer Composition (wt %) | | | | | | | | Tensile strength (g/2.5 cm) | | Heat Sealability (g/5 cm) | | Runnability |
| --- | --- | --- | --- | --- | --- | --- | --- | --- | --- | --- | --- | --- | --- |
| | BA | St | IA | AA | MAA | AM | HEMA | MOA | Dry | Wet | Dry | Wet | |
| Comparative 1 | 77 | 19.5 | | | 2 | | | 1.5 | 930 | 350 | 0 | 0 | Good |
| Comparative 2 | 77 | 20 | 3 | | | | | | 290 | 120 | — | — | Poor |
| Comparative 3 | 67 | 30 | | | 3 | | | | 630 | 100 | 370 | 270 | Good |
| Comparative 4 | 72 | 25 | | | 3 | | | | 600 | 120 | 300 | 250 | V. Good |
| Comparative 5 | 77 | 21 | | | 2 | | | | 640 | 130 | 300 | 190 | Bad |
| Comparative 6 | 77 | 19.5 | | | 2 | 1.5 | | | 690 | 190 | 120 | 70 | V. Good |
| 7 | 78 | 20 | 2 | | | | | | — | 370 | 410 | 490 | Poor |
| 8 | 78.5 | 19.5 | 1.5 | | 1 | | | | 870 | 310 | 180 | 160 | Poor |
| 9 | 77 | 20 | 1.5 | | 1.5 | | | | — | 320 | 300 | 310 | Good |
| 10 | 78 | 20 | 1.5 | | 0.5 | | | | — | 360 | 310 | 280 | Poor |
| 11 | 77.5 | 20 | 1.5 | | 1 | | | | — | 340 | 440 | 400 | V. Good |
| 12 | 71.9 | 24.5 | 1.8 | | 1.8 | | | | — | 290 | 560 | 530 | V. Good |
| 13 | 78 | 20 | 1 | 1 | | | | | 690 | 410 | — | — | Good |
| 14 | 77 | 20 | 1.5 | 1.5 | | | | | 720 | 520 | 250 | 230 | V. Good |
| 15 | 77 | 20 | 1 | 2 | | | | | 810 | 430 | — | — | Good |
| 16 | 77 | 20 | 2 | 1 | | | | | 810 | 400 | — | — | Good |
| 17 | 76 | 20 | 2 | 2 | | | | | 820 | 400 | — | — | Good |
| 18 | 75.5 | 20 | 1.5 | 3 | | | | | 850 | 510 | 160 | 170 | Good |
| 19 | 77.5 | 20 | 1 | | | 1.5 | | | 1000 | 420 | — | — | Poor |
| 20 | 72 | 25 | 1.5 | | | 1.5 | | | 830 | 340 | 130 | 110 | V. Good |
| 21 | 77 | 20 | 1.5 | | | 1.5 | | | 800 | 360 | 40 | 35 | V. Good |
| 22 | 71 | 25 | 1.5 | 1 | | 1.5 | | | 750 | 290 | 100 | 80 | V. Good |
| 23 | 76 | 20 | 1.5 | 1 | | 1.5 | | | — | 350 | 95 | 90 | V. Good |
| 24 | 75.5 | 20 | 1.5 | 1.5 | | 1.5 | | | — | 330 | 180 | 160 | V. Good |
| 25 | 77 | 20 | 1.5 | 1 | | 0.5 | | | — | 365 | 200 | 250 | V. Good |
| 26 | 72 | 25 | 1.5 | | | | 1.5 | | — | 280 | — | 60 | V. Good |
| 27 | 76 | 20 | 1.5 | 1 | | | 1.5 | | — | 250 | 80 | 60 | V. Good |

Key:
BA = butyl acrylate;
St = Styrene;
IA = Itaconic acid;
AA = acrylic acid;
MAA = Methacrylic acid;
AM = acrylamide;
HEMA = hydroxyethylacrylate;
MOA = N—methylolacrylamide

HEAT-SEALABILITY

58–62% solids of the binder are applied by impregnation, as for the tensile strength test, using a bath concentration of about 20% solids. The samples are dried and cured for 2 minutes at 150° C. From the impregnated webs, samples 5×7.5 cm are taken from the machine direction and sealed as follows:

Two 0.6 cm (¼ inch) wide strip seals of 5 cm length are made using a Bland Heatsealing apparatus on a doubled non-woven sample. The samples are then conditioned as above and tested in the Instron machine for peel strength dry and wet after soaking for 30 seconds in water. An average of 8 tests are taken with Instron settings as above and the heatsealing apparatus settings of 2.8 kg/m² (40 psi), 200° C. and 0.3 seconds.

RUNNABILITY

The copolymer emulsion is diluted 50:50 with water. 0.1% Nopco DF-16OL is added and the pH adjusted to 9. A Benz padder is modified so that the bottom roller of the vertical padder runs constantly in the prepared formulation. The padder is run for 2 hours at a speed of 31 m/min. and a pressure of 45 kg/cm². The bath level is kept constant by addition of water and the build-up on the apparatus is rated visually.

EXAMPLES 28–35

Non-woven fabrics are prepared from 100% rayon, examples 28–32, and 50/50 weight % rayon/polyester, examples 33–35. The fabrics are bound by the polymers described in Table 2. It should be noted that the tensile results in this table are not directly comparable with the results given in Table 1.

The Table illustrates comparative examples 28 and 33, in which the binder contains methylol groups, and example 29, in which the binder is free from methylol groups and dicarboxylic acid. It can be seen from the other examples in the table that the presence of dicarboxylic acid gives comparable wet strength and that the combination of dicarboxylic and monocarboxylic acids gives comparable wet abrasion and wet strength, when compared with the methylol-containing binder.

In Table 2 the following test methods are used:

TENSILE STRENGTH

The webs of the specified fibre type are supported between two layers of glass fibre scrim and saturated in 6% polymer solids baths on a Birch Brothers Padder at 18.14 kg (40 lbs) nip roll pressure with a speed of 6.95 m/min. The padded webs are dried for 7 minutes at 65.5° C. (150° F.) in a forced air oven, and cured for 1.5 minutes at 150° C. The finished fabrics have a dry weight of 23–26 g/m² and contain 30% binder.

Specimens are cut to 2.5 cm × 15.2 cm in the machine direction and tested in an Instron machine with a jaw separation of 12.7 cm and an extension rate of 5.1 cm/min. Wet strength is determined after soaking the samples in water for 30 minutes.

WET ABRASION RESISTANCE

Non-woven samples, prepared as described in the tensile strength test, are subjected to repeated washings in a Maytag washing machine using no soap. The machine is set on full hot (140° C.) water cycle and contains eight terrycloth towels as ballast. Failure is noted when a web splits into two pieces. Each composition is run twice.

HAND

Hand, or softness, is determined on fabrics prepared as described in the tensile strength test above. A panel of six people rate the fabrics from 1 (soft) to 5 (staff). The highest and lowest ratings for each fabric is ignored and the remainder averaged to give the final ranking.

TABLE 2

| Example | Fibre Type (wt %) | Monomer Composition (wt %) | | | | | | Wet Abrasion Resistance (Washes survived) | Wet Tensile Strength (g/2.5 cm) | HAND |
|---|---|---|---|---|---|---|---|---|---|---|
| | | Ba | St | MAA | IA | AA | MAA | MOA | | | |
| Comparative 28 | 100% rayon | 77 | 19.5 | | | | | | 25 | 952 | 3.8 |
| Comparative 29 | 100% rayon | 60 | 38 | | | 2 | | | 5 | 1225 | 1.4 |
| 30 | 100% rayon | 60 | 38 | 2 | | | | | 10 | 1451 | 2.6 |
| 31 | 100% rayon | 77 | 20 | | 1.5 | 1.5 | | | 25 | 1814 | 1.3 |
| 32 | 100% rayon | 77 | | 20 | 1.5 | 1.5 | | | 25 | 952 | 3.0 |
| Comparative 33 | 50/50 rayon/polyester | 77 | 19.5 | | | | 2 | 1.5 | 25 | 1179 | 2.7 |
| 34 | 50/50 rayon/polyester | 77 | 20 | | 1.5 | 1.5 | | | 25 | 1088 | 3.8 |
| 35 | 50/50 rayon/polyester | 77 | | 20 | 1.5 | 1.5 | | | 22 | 726 | 2.8 |

Key:
for monomer symbols see key to Table 1

We claim:
1. A non-woven fibrous product whose fibres comprise at least 50%, by weight of dry fibre weight, of hydrophilic fibres, as hereinbefore defined, in which the fibres are bonded together by an emulsion copolymer of a monomer composition comprising:
   (a) 50–80% of the total monomers of at least one $C_4$–$C_8$ ester of acrylic and/or methacrylic acid;
   (b) 10–49% by weight of the total monomers of at least one of methyl methacrylate, styrene and α-methyl styrene; and
   (c) 0.5–10% by weight of the total monomers of acid comprising at least one monoethylenically unsaturated dicarboxylic acid, optionally in combination with at least one monoethylenically unsaturated monocarboxylic acid;
the copolymer being free from units containing methylol groups and free from added aminoplasts.

2. A product as claimed in claim 1, wherein the fibres comprise at least 50% by weight of dry fibre weight of cellulosic fibres and the balance, if any, one or more other natural or synthetic fibres.

3. A product as claimed in claim 2, wherein the fibres are 100% rayon.

4. A product as claimed in claim 3, wherein the fibres are bonded together by an emulsion copolymer of a monomer composition comprising:
   (a) 60–80% by weight of the total monomers of at least one $C_4$–$C_8$ alkyl ester of acrylic and/or methacrylic acid;
   (b) 15–30% by weight of the total monomers of at least one of methyl methacrylate, styrene and α-methyl styrene;
   (c) 1–6% by weight of the total monomers of acid comprising at least one monoethylenically unsaturated dicarboxylic acid, optionally in combination with at least one monoethylenically unsaturated monocarboxylic acid.

5. A product as claimed in claim 4, wherein component (c) comprises 0.5–3% by weight of the total monomers of at least one monoethylenically unsaturated dicarboxylic acid and 0.5–3% by weight of the total monomers of at least one monoethylenically unsaturated monocarboxylic acid.

6. A product as claimed in claim 5 wherein component (c) comprises itaconic acid and acrylic and/or methacrylic acid.

7. A product as claimed in claim 6 wherein the copolymer consists substantially of units of butyl acrylate, styrene, itaconic acid and acrylic and/or methacrylic acid.

8. A product as claimed in claims 2 or 3 in the form of diaper coverstock or a finished diaper.

9. A product as claimed in claim 7 in the form of diaper coverstock or a finished diaper.

* * * * *